(12) United States Patent
Sandström et al.

(10) Patent No.: US 9,271,490 B2
(45) Date of Patent: Mar. 1, 2016

(54) COMPOSITIONS

(71) Applicant: Krefting & Sandström Lifeclean AB, Uddevalla (SE)

(72) Inventors: Staffan Sandström, Stockholm (SE); Carl-Gustav Millinger, Stockholm (SE)

(73) Assignee: LIFECLEAN INTERNATIONAL AB, Uddevalla (SE)

( * ) Notice: Subject to any disclaimer, the term of this patent is extended or adjusted under 35 U.S.C. 154(b) by 0 days.

(21) Appl. No.: 14/183,314

(22) Filed: Feb. 18, 2014

(65) Prior Publication Data

US 2014/0234441 A1  Aug. 21, 2014

(30) Foreign Application Priority Data

Feb. 19, 2013  (GB) .................................. 1302867.5

(51) Int. Cl.
*A01N 25/30* (2006.01)
*A01N 59/00* (2006.01)
*A61L 12/10* (2006.01)
*A61L 2/18* (2006.01)

(52) U.S. Cl.
CPC ................ *A01N 25/30* (2013.01); *A01N 59/00* (2013.01); *A61L 12/102* (2013.01); *A61L 2/18* (2013.01)

(58) Field of Classification Search
CPC ...... A01N 25/30; A01N 59/00; A61L 12/102; A61L 2/18
See application file for complete search history.

(56) References Cited

U.S. PATENT DOCUMENTS

| 4,889,654 A | 12/1989 | Mason et al. |
| 2002/0002125 A1* | 1/2002 | Colurciello, Jr. et al. ..... 510/238 |
| 2008/0067470 A1 | 3/2008 | Thangaraj et al. |
| 2009/0028965 A1 | 1/2009 | Healey |

FOREIGN PATENT DOCUMENTS

| EP | 0175826 A1 | 4/1986 |
| EP | 2130794 A1 | 12/2009 |
| JP | 2005-281651 A | 10/2005 |
| WO | 92/14190 A1 | 8/1992 |
| WO | 2009/021557 A1 | 2/2009 |

OTHER PUBLICATIONS

Lin et al., Disinfection effect of chlorine dioxide on air quality control in Armed Forces General Hospital of Taiwan, 2007, Nature and Science, 5 (4), pp. 94-99.*
Combined Search and Examination Report from corresponding GB 1302867.5 dated Aug. 7, 2013.
English Translation of Official Action dated Sep. 15, 2015 from corresponding Japanese Application No. 2014-027208.

* cited by examiner

*Primary Examiner* — Trevor Love
(74) *Attorney, Agent, or Firm* — Porter, Wright, Morris & Arthur LLP; Holly Kozlowski

(57) ABSTRACT

Acidic aqueous compositions for elimination of spores of spore forming bacteria comprise from about 100 to about 2000 ppm dissolved chlorine dioxide and a surfactant system having both a wetting effect and a spore solubilising effect.

9 Claims, No Drawings

COMPOSITIONS

FIELD OF INVENTION

The present invention is directed to new compositions of chlorine dioxide adapted to be effective for inhibiting spore forms of bacteria.

BACKGROUND OF THE INVENTION

Chlorine dioxide is a well-known disinfecting agent and has been used for water cleaning and water processing since the 1950s. Chlorine dioxide is notorious labile compound as it is a powerful oxidizing agent. As chlorine dioxide generally is regarded as unstable during storage in aqueous solutions, numerous technical disclosures advice systems and devices how to produce chlorine dioxide at the point of use. One commonly employed is to combine a solution of sodium chlorite with a strong acidic solution, for example comprising hydrochloric acid in order to produce immediately applicable chlorine dioxide formulations. WO 2007/079287 (CDG Technology Inc.) discloses methodologies to stabilize dilute chlorine dioxide solutions in order to prolong product shelf life. WO2009/058530 (Ecolab) discloses compositions exhibiting low concentrations of chlorine dioxide together with an anionic surfactant, which demonstrate efficacy for inactivating coccidian parasites.

US Patent application 2009/0028965 (Clinimax Limited) discloses a multi-part composition capable of generating a chlorine dioxide solution at point use. The resulting compositions comprise, besides dilute chlorine dioxide, sodium lauryl sulphate as a detergent and hold a pH at about 5.0. Even if this document allegedly exhibits promising results, related products and other chlorine dioxide releasing products appear to have limited effects on spores of *Clostridium difficile* when tested in health care environmental sites, see S D Goldenberg et al. in Journal of Hospital Infection, 2012, Vol. 82, pp. 64-67. The problem is also confirmed by S. Ali et al in Journal of Hospital Infection, 2011 Vol. 79, pp 78-79, wherein it is reported that commercial sporicidal preparations fail to satisfyingly eliminate spores on surfaces even if they apparently meet sporicidal requirements when tested on spore suspension tubes. It is evident that there both is a lack of effective disinfectants and also test methodologies to ascertain effectiveness against surface associated spores from *Clostridium difficile* and similar pathologic spore forming organisms.

It would therefore be strongly desirable to provide suitably stable and dilute chlorine dioxide solutions adapted to effectively inhibit also spores of virulent spore forms of virulent bacteria, such as *Clostridium difficile* on surfaces in hospital environments. Advantageously, such disinfective solution should be safe to store and handle, while being convenient to administer at exposed surfaces, also in populated hospital environments without needing any relocation to specifically designated sanitization areas, while counteracting corrosiveness and considering general hygienic limits for chlorine dioxide.

DESCRIPTION OF THE INVENTION

In most general terms the present invention is directed to acidic aqueous compositions for elimination of spores of spore forming bacteria, comprising from about 100 to about 2000 ppm dissolved chlorine dioxide, a surfactant system having both a wetting effect and a spore solubilising effect. Other representative examples of concentration ranges of chlorine dioxide for the compositions of the invention are about 100 to about 1600 ppm; about 100 to about 1000 ppm; and about 500 to about 1000 ppm. Examples of suitable concentrations of chlorine dioxide in composition according to the invention are about 100 ppm, about 200 ppm about 300 ppm, about 400 ppm, about 500 ppm , about 600 ppm, about 700 ppm, about 800 ppm, about 900 ppm, about 1000 ppm, about 1100 ppm about 1200 ppm, about 1300 ppm about 1400 ppm, about 1500 ppm and about 1600 ppm, In this respect the term "about" represents the fact since the concentration of chlorine dioxide in the composition products may slightly decay from their manufacturing to their use. The compositions generally have a pH of about 1 to about 4. The compositions are inventively adapted to eliminate spores of bacteria in particular bacteria species of the genus *Clostridium*, such as *Clostridium difficile* on surfaces on objects made of glass, wood, metal and various plastic materials in particular of surfaces in hospital environments. The compositions are especially adapted to eliminate spores which adhere to cavities, or microcavities or other irregular surface structures that are difficult to reach with conventional disinfectants. The compositions are further adapted to minimize environmental impact during the disinfection process, while maximizing their disinfection capacity even at short contact times below 10 minutes. The term eliminating does in the context of the present invention mean that the spores are destroyed and do not survive to replicate.

For these purpose, the compositions comprise an effective amount of chlorine dioxide with a capacity of exerting a suitably powerful oxidative attack on the spore and system of surfactants comprising surfactants with different complementary effects by supporting the disinfecting capacity of chlorine oxide, also in comparatively low concentrations. Accordingly, the inventive compositions comprise at least one surfactant with a capacity to contribute to a wetting effect of the composition and at least one surfactant that contribute to a spore solubilising effect.

In this context a "wetting effect" means that the compositions are capable is readily applicable to administer to the surface and to distribute to the surface to form cohesive films. In the meaning of the present invention, "wetting effect" contributes to that the chlorine dioxide composition is suitably distributed to cavities of the surfaces in order to enable suitable elimination contact between dissolved chlorine dioxide and spores.

Also, in all contexts of the invention "solubilising effect" means that the compositions are capable reduce or eliminate the adhesion of the spores to the surface. The "solubilising effect" is related to effect of "general detergency" of the compositions which would include removing the spores from surface, contributing to support contact with chlorine dioxide and make the spores liable for a chemical oxidative attack.

Further in this context, the terms that a surfactant contributes to "wetting effect" does not exclude that it has also a certain "solubilising effect and vice versa. The intended meaning is that at least one surfactant have more pronounced contribution to a wetting effect than a solubilising effect and that at least on surfactant has a more pronounced solubilising effect than a wetting effect.

Further in general terms, in order to meet the requirements of effectively provide a wetting effect and a solubilising effect in the specific recited chlorine dioxide containing compositions, the surfactant system comprises two or more hydrocarbon ionic surfactants stable for oxidation at an acidic pH of about 1 to about 4, of which at least two surfactants have a difference in hydrocarbon chain length. An example of a suitable difference is at least four carbon atoms.

"Hydrocarbon ionic surfactants" is defined in this context that they are ionic at an acidic pH and that they comprise a straight or branched hydrocarbon chain. The hydrocarbon chain may be saturated or unsaturated and thereby termed straight or branched alkyl, alkenyl or alkynyl. The hydrocarbon chain may further be substituted with groups that contribute to or improve any surface activity or induce stability. The hydrocarbon chain can further be interrupted with one or more heteroatoms, as exemplified by alkoxy chains. In the context of ionic surfactants, the skilled artisan will have a clear understanding of what signifies a hydrocarbon chain and that different brands of surfactants based hydrocarbon ionic surfactants can vary the chain length, when based on the same chemical structures providing the ionic groups.

In this context "stability" means that the surfactants are not substantially degraded in an acidic pH of about 1-4 and that they are not liable for oxidation by chlorine dioxide, i.e. "chlorine dioxide stable". In other terms stability means substantially stable from chemical degradation also during shipping and storage, but also from any form of physical destabilization in the solution, such as precipitation, clouding or any other phenomena that affects surfactant functionality or any general visual appearance of the compositions.

In a general aspect, the compositions with chlorine dioxide according to the invention includes a surfactant system comprising two or more hydrocarbon ionic surfactants stable for oxidation at an acidic pH, wherein at least two surfactants having hydrocarbon chains with different chain lengths in order to provide the surfactant system with the mentioned, desirable characteristics.

In one aspect, the compositions according to the invention pertains to an acidic aqueous composition having a pH of from about 1 to about 4, for elimination of spores of spore forming bacteria, comprising from about 100 to about 2000 ppm dissolved chlorine dioxide, a surfactant system having wetting effect and a spore solubilising effect, wherein the surfactant system comprises at least two hydrocarbon ionic surfactants stable for oxidation at a pH of about 1 to about 4, of which said at least two surfactants have a difference in hydrocarbon chain length of at least four carbon atoms.

In one aspect, the composition two or more surfactants are present in amount of from about 0.01 to about 2% (v/v), exemplified with to 0.02 to about 2% (v/v)about 0.1 to about 1% (v/v).

In one aspect, two or more surfactants are cationic surfactants at a pH in the range of from about 1 to about 4.

In one aspect, the compositions according to the invention comprise two or more cationic surfactants include amine oxides stable at the low pH and in presence of chlorine dioxide. Amine oxides suitable for use in the present invention include alkyl di(lower alkyl) amine oxides in which the alkyl groups can have 6-20 carbon atoms, preferably, 8-18 carbon atoms and can have a straight or branched chain that is saturated or unsaturated, The lower alkyl groups have from 1 to 7 carbon atoms. Examples include C-8 and C-12 amine oxides and in one aspect that the compositions include one surfactant that is a C-8 amine oxide and one surfactant that is a C-12 amine oxide. Examples of such surfactants include octyldimethylamine oxide and lauryldimethylamine oxide.

Alternative amine oxides include alkyl (dihydroxy lower alkyl) amine oxides, wherein the alkyl groups can have 6-20 carbon atoms, preferably, 8-18 carbon atoms and can have a straight or branched chain that is saturated or unsaturated. The lower alkyl groups have from 1 to 7 carbon atoms.

Still alternative amine oxides include alkylmorpholine oxides having alkyl groups with 6-20, preferably 6 to 12 carbon atoms.

In one aspect of the invention, the compositions comprise from about 100 to about 2000 ppm chlorine dioxide, from about 0.1 to about 2 (v/v)% of two cationic surfactants having hydrocarbon chains with different chain lengths in order to establish both a wetting effect and a solubilising effect, as discussed above, the cationic surfactants can be present in the composition in an equal amount or an about equal amount. The cationic surfactants can differ in chain length with four carbon atoms, or more.

In one aspect, the composition comprise from about 100 to about 1600 ppm chlorine dioxide, and the amount of surfactants are about 0.2% (v/v) which comprise essentially equal amounts of octyldimethylamine oxide and lauryldimethylamine oxide.

In one aspect of the invention, the composition includes the two or more surfactants which are anionic surfactants, stable at a pH in the range of from about 1 to about 4. The anionic surfactants are selected so as to contribute both to a wetting effect and a solubilising effect.

In one aspect of the invention, the compositions comprise from about 100 to about 1600 ppm chlorine dioxide, from about 0.1 to about 1 (v/v)% of two anionic surfactants having hydrocarbon chains with different chain lengths in order to establish both a wetting effect and a solubilising effect, as discussed above, the anionic surfactants can be present in the composition in an equal amount or an about equal amount. The anionic surfactants can differ in chain length with four carbon atoms, or more.

In one aspect of the invention, the two more anionic surfactants are selected from group consisting of soluble salts of alkyl sulphates, alkyl sulphonates, alkyl aryl sulphonates (alkylbenzene sulphonates), and aryl sulphonates having from 6 to 25 carbon atoms in the alkyl chains, or between 8 to 19 carbon atoms in the alkyl chains.

In one aspect, the anionic surfactants are sodium salts of alkyl-diphenyloxide-disulphonates or alkyl-phenyl/diphenyl-sulphonates with 6 to 19 carbon atoms in the alkyl chains. One example of anionic surfactant is alkyl diphenyloxide disulphonate and/or alkyl(sulphophenoxy)benzene sulphonate. One example is decyl(sulfophenoxy)-disodium salt as included in the product sold by Dow Chemical Company under the tradename Dowfax 3B2. One example is mono- and dihexadecyl disulphonted diphenyl oxide disodium salt as included in the product sold by Dow Chemical Company under the tradename Dowfax 8390.

In one aspect the invention relates to a method of elimination the spores of spore forming bacteria on a surface by contacting the surface with a composition comprising chlorine dioxide in an effective amount and two more surface active agents in a surfactant system, wherein at least one surface active agent contributes to a wetting effect in order to safely and cohesively distribute the composition to all parts of a surface, while at least one surface active agent shall contribute to solubilising effect of the spores in the meaning directly or indirectly affect the spore surfaces in order make the spores more liable for the effects of the chlorine dioxide. In this context an effective amount means any concentration or concentration range referred to in this specification. Also in this context, the at least two surface active agents can be selected as outlined and used with any exemplified composition in the previous parts of this specification. In particular, at least two surfactants shall have significant difference in hydrocarbon chain length which means a difference of from 2 to 12 carbon groups. An exemplifying difference is 4 carbon groups. Further in this context, contacting a surface includes any administration or application of a composition according to the invention to the surface in order to or with the purpose to sufficiently cover a surface contaminated, or regarded to be at risk to be contaminated with spores. An especially preferred usefulness of the method is the elimination of spores from the genus *Clostridium*, especially *Clostridium difficile*.

In one aspect of the described methods, the elimination of spores of spore forming bacteria on a surface are directed to contacting the surface a sufficient amount of any composition as previously disclosed during a limited contact time, such as 10 minutes or less, or a contact time such as 9 minutes, 8 minutes 7 minutes, 6 minutes, 5 minutes, 4 minutes, 3 minutes, 2 minutes, 1 minute or less such as 30 seconds or less.

Without being bound to any particular theory, it is apparent that the present invention comprising chlorine dioxide and in combination with the described systems of different surfactants with complementary effects appears necessary for elimination of spores associated with surfaces. In addition to an adequate wetting effect for distributing the composition to all parts of the surfaces, a detergency effect is obtained by which adhesion between the spores and surfaces is abolished. In addition, the compositions according to the invention appear to have a solubilising effect directly on the spore surface which results in loss of integrity of the spores and may render them susceptible for and enhance the oxidative attack of chlorine dioxide.

In the following exemplifying part tests are outlined with compositions and methods of the invention that verify the efficacy to eliminate spores on surfaces at very rigorous conditions at levels of contamination designed to exceed conditions normally encountered in clinical environments even during epidemic events.

DETAILED AND EXEMPLIFYING DESCRIPTION

EXAMPLE 1

Manufacturing of Chlorine Dioxide Compositions

Chlorine dioxide cannot be conventionally stored as a gas due to its explosiveness, but is generally highly soluble in water. Chlorine dioxide is however extremely volatile and it has remained a problem to manufacture, ship and store concentrated chlorine dioxide solutions without significant losses. In the context of the present invention aqueous chlorine dioxide compositions can be produced according to different protocols as outline in EPA Guidelines Manual Alternative Disinfectants and Oxidant, April 1999, Chapter 4. Chlorine Dioxide, pages 4-1 to 4-41.

For the purpose of producing compositions having from 100 to 2000 ppm dissolved chlorine dioxide of the present invention, chlorine dioxide is generated by mixing 9% (w/v) HCl and 7% (w/v) $NaClO_2$ (sodium chlorite) which rapidly reacts to form chlorine dioxide $ClO_2$ and NaCl in a highly acidic environment.

A prototype stock solution of 5 liters comprising approx. 1600 ppm chlorine dioxide was prepared by mixing 300 ml 9% (w/v) HCl and 300 ml 7% (w/v) $NaClO_2$ (sodium chlorite) diluted with 4.4 liters highly purified water (Millipore Milli-Q).

In order to balance out the decay of concentration between the moment of production and moment of surface tests according to following examples, a stock solution was made with an intended surplus of chlorine dioxide of about 10-20%. For this reason, the concentration values of the exemplified solutions during the tests raging from 100-1600 ppm shall be regarded as nominal and may vary up to 20%, such as 10-20% from their indicated concentration values.

EXAMPLE 2A

A solution for Testing was Produced From the Stock Solution by Mixing
1800 mL stock solution.
1.8 mL Macat(RTM) AO-8 (approx. 30% Octyl Dimethylamine Oxide)
1.8 mL Macat(RTM) AO-12 (approx. 30% Lauryl Dimethylamine Oxide)
to a test solution of a pH of approximately 1 with approximately 1600 ppm chlorine dioxide, including about 0.1% (v/v) AO-8 and about 0.1% (v/v) AO-12.

EXAMPLE 2B

A number of test solutions were generated from the stock solution produced according to Example 1 with the cationic surfactants of Example 2 with different levels of chlorine dioxide.

Aliquotes from the solution in example 2 was further diluted 2, 4, 8, 16 times with MilliQ-water containing about 0.1% (v/v) AO-8 and 0.1% (v/v) AO12. The final set of test solutions contained 1600, 800, 400, 200 and 100 ppm $ClO_2$ with a total amount of surfactant of 0.2% (v/v).

EXAMPLE 3

A second solution for testing was produced from the stock solution by mixing 1000 ml stock solution with 1 mL DOWFAX(RTM) 3B2 (approx 38% Benzenesulfonic acid, decyl (sulfophenoxy)-, disodium salt and approx 8% Benzenesulfonic acid, oxybis(decyl)-, disodium salt and 1 mL DOWFAX(RTM) 8390 (38.5% % Mono- and dihexadecyl disulphonted diphenyl oxide disodium salt) to a test solution of a pH of approximately 1, including approximately 1600 ppm chlorine dioxide.

EXAMPLE 4

In this example, a methodology is outlined to investigate if compositions according to present invention exhibit an elimination capacity for spore forming bacteria on surfaces. The example also compares with conventional anti-bacterial agents and confirms their relative inefficacy.
Elimination of spores of *Clostridium difficile* on surfaces
Methods and Materials
Spore Suspension

*C difficile* spores PCR Ribotype 023 (ECDC/Cardiff nomenclature) were transferred from a frozen sample to plates with Fastidious Anaerobe Agar (FAAAP), cultured under anaerobe conditions for 2 days. The cultures were transferred to ambient conditions and colonies of *C difficile* were admitted to sporulate. The spores were harvested and dissolved in sterile water (reverse osmosis (RO)), subjected to alcohol shock (70%), washed, centrifugated and collected as a suspension of spores. The Spores were counted in a Bürker chamber to $2.4 \times 10^8$ spores (i.e. spores on the tested surfaces) comparing with approximately 80% spores in the suspension.
Agar Plates In the experiment Fastidious Anaerobe Agar (FAAAP) was with added taurocholate (1 g/l), except from control of the filtrate, where agar plates selective for *C. difficile* was used.

Preparation of Surfaces

In the preparation 0.1 ml of the spore suspension was transferred to microscopy slides, sterile plates of brass or copper. When the spore suspensions have dried, 0.2 ml of the following solutions were added:
A solution made in accordance with Example 2A
Virkon 1%
Ethanol 70%
Sterile RO-water After 10 minutes exposure to the solutions, the Glasses and the plates were each transferred to a 500 ml Glass flask to dilute and interrupt disinfection. The flasks were rotated at 200 rpm for 20 minutes.

Culturing

From each of the rotated flasks 0.1 ml was transferred to agar plates (Culture 1). The samples were diluted in two steps 1/10 in tubes. From each tube, 0.1 ml was transferred to agar plates (Cultures 2 and 3).

The solutions in the flasks were filtered and rinsed with 3 x 100 ml buffered peptone water (PENAL). The filtrations were performed in two steps. At first, 1 ml was filtered, then remaining volume of solution in the flasks (approx. 249 ml). The filters were cultured on agar plates (Cultures 4 and 5).

At two times, 40 ml samples were taken from the filtrates. These were centrifugated and the supernatant was discarded, the pellet re-suspended in 0.1 ml 0.85% NaCl solution. The entire volume was transferred to agar plates.

In order to assess if viable spore remain on the surfaces of Glasses and the, they were smeared with moist cotton tip (all smeared in accordance with a "double-S" shape). The tip was cultured in 2 ml pre-reduced PY-broth which was diluted 1/10 in several repeated steps and cultured on agar plates (0.2 ml/plate), (Cultures 6 to 9)

All culture plates were cultured under anaerobe conditions at 36° C. for 2 days.

The results are demonstrated in Table 1, below.

In Table 1, results are demonstrated for Culture 1 to 9 for the three different surfaces (Glass, brass, copper) with the four different test solutions. The results within brackets refer to total amount of CFUs (colony forming units) in the flasks, i.e. the amount of spores that have survived treatment with the tests solutions and have been displaced from the surfaces during rotation of the flasks. Table 1 also demonstrates the amount of CFU in the undiluted PY-broth referring the amount of spores surviving treatment of the test solution, but have remained attached to the surface during rotation of flasks.

Table 1 demonstrates that the test solution referring to Example 2 has excellent capacity to eliminate spores of *C difficile*. It is also significant that the test solution according to Example 2A has capacity to eliminate spores which adhere to a surface and thereby would be difficult to eliminate or less susceptible for conventional elimination agents.

In addition to the results of Table 1, it was confirmed that no growth was found in the cultures from the samples taken from the filtrate.

TABLE 1

|  | Culture 1<br>0.1 mL<br>From bottle | Culture 2<br>Dilution<br>$10^{-1}$ | Culture 3<br>Dilution<br>$10^{-2}$ | Culture 4<br>Filtration<br>1 mL | Culture 5<br>Filtration<br>249 mL | Culture 6<br>PY-broth<br>undiluted | Culture 7<br>PY-broth<br>$10^{-2}$ | Culture 8<br>PY-broth<br>$10^{-4}$ | Culture 9<br>PY-broth<br>$10^{-6}$ |
|---|---|---|---|---|---|---|---|---|---|
| RO-water<br>Glass | overgrown | 527 | 53<br>$(1.3 \times 10^7)$ | overgrown | overgrown | overgrown | overgrown | 24<br>$(2.4 \times 10^6)$ | 3 |
| RO-water<br>Brass | overgrown | 254<br>$(6.4 \times 10^6)$ | 23 | overgrown | overgrown | overgrown | overgrown | 45<br>$(4.5 \times 10^6)$ | 1 |
| RO-water<br>Copper | overgrown | 155<br>$(3.9 \times 10^6)$ | 14 | overgrown | overgrown | overgrown | overgrown | 62<br>$(6.2 \times 10^6)$ | 1 |
| Virkon 1%<br>Glass | overgrown | 189<br>$(4.7 \times 10^6)$ | 10 | overgrown | overgrown | overgrown | overgrown | 94<br>$(9.4 \times 10^6)$ | 0 |
| Virkon 1%<br>Brass | 461<br>$(1.1 \times 10^6)$ | 32 | 2 | overgrown | overgrown | overgrown | overgrown | 13<br>$(1.3 \times 10^6)$ | 0 |
| Virkon 1%<br>Copper | overgrown | 68<br>$(1.7 \times 10^6)$ | 2 | overgrown | overgrown | overgrown | overgrown | 15<br>$(1.5 \times 10^6)$ | 0 |
| Example<br>2A Glass | 0 | 0 | 0 | 0 | 4 | 0 | 0 | 0 | 0 |
| EXAMPLE<br>2A Brass | 0 | 0 | 0 | 0 | 84 | 0 | 0 | 0 | 0 |
| EXAMPLE<br>2A Copper | 0 | 0 | 0 | 0 | 9 | 0 | 0 | 0 | 0 |
| 70% Ethanol<br>Glass | overgrown | 517<br>$(1.2 \times 0^7)$ | 46 | overgrown | overgrown | overgrown | overgrown | 39<br>$(3.9 \times 10^6)$ | 1 |
| 70% Ethanol/<br>Brass | overgrown | 55<br>$(1.4 \times 10^6)$ | 5 | overgrown | overgrown | overgrown | overgrown | 74<br>$(7.4 \times 10^6)$ | 0 |
| 70% Ethanol<br>Copper | 429 | 40<br>$(1.0 \times 10^6)$ | 1 | overgrown | overgrown | overgrown | overgrown | 79<br>$(7.9 \times 10^6)$ | 0 |

EXAMPLE 5

Sterile microscopy slides (glass surfaces) with spore suspension were prepared in accordance with Example 4.

The solutions prepared in Example 2B containing 1600, 800, 400, 200 and 100 ppm $ClO_2$ with a total amount of surfactant of 0.2% (v/v) were applied to the glass surfaces in accordance with Example 4.

The glass slides were treated in the same way as in Example 4 and samples were taken and cultured in the same way as in Example 4.

The results are demonstrated in Table 2 for the solutions comprising 1600, 800, 400, 200 and 100 ppm $ClO_2$ The results are presented in the same way as in Table 1.

It is evident that compositions according to the invention having so low concentrations of chlorine dioxide as 100 ppm have an improved efficacy of eliminate spores of *C difficile*, compared to conventional agents, such as ethanol and Virkon. The results also indicate that compositions according to the invention have capacity to exert its effect on different types of surfaces.

In addition to the results of Table 1, it was confirmed that no growth was found in the cultures from the samples taken from the filtrate.

Example 3 branded DOWFAX 3B2 and DOWFAX 8390, respectively. RD3 and RD4 signify the cationic surfactants of Example 2A branded AO-8 Macat and AO-12 Macat.

TABLE 2

|  | 0.1 mL From bottle | Dilution $10^{-1}$ | Dilution $10^{-2}$ | Filtration 1 mL | Filtration 249 mL | PY-broth undiluted | PY-broth $10^{-2}$ | PY-broth $10^{-4}$ | PY-broth $10^{-6}$ |
|---|---|---|---|---|---|---|---|---|---|
| RO-water I | overgrown | overgrown | 170 ($4.2 \times 10^7$) | overgrown | overgrown | overgrown | overgrown | 200 ($2.0 \times 10^7$) | 4 |
| RO-water II | overgrown | overgrown | 107 ($2.7 \times 10^7$) | overgrown | overgrown | overgrown | overgrown | 177 ($1.8 \times 10^7$) | 0 |
| 100 ppm | 130 ($3.2 \times 10^5$) | 8 | 1 | overgrown | overgrown | overgrown | overgrown | 159 ($1.6 \times 10^7$) | 1 |
| 200 ppm | 57 ($1.42 \times 10^5$) | 3 | overgrown | overgrown | overgrown | overgrown | overgrown | 67 ($6.7 \times 10^6$) | 0 |
| 400 ppm | 18 | 0 | 0 | 108 ($2.7 \times 10^7$) | overgrown | overgrown | overgrown | 27 ($2.7 \times 10^3$) | 0 |
| 800 ppm | 0 | 0 | 0 | 9 ($2.2 \times 10^3$) | 1000 | 16 ($1.6 \times 10^3$) | 0 | 0 | 0 |
| 1600 ppm | 0 | 0 | 0 | 0 | 38 ($3.8 \times 10^3$) | 0 | 0 | 0 | 0 |

EXAMPLE 6

Example 6 was designed in order to evaluate different types and combinations of surface active agents in combination with chlorine oxide for elimination of spores of *C Difficile* on surfaces. The following test solutions were used:
Sterile RO-water
Ethanol 70%
Solution LC1 comprising: 1600 ppm chlorine dioxide
Solution LC1_12 comprising: 1600 ppm chlorine dioxide with 0.2% (v/v) RD1 and RD2
Solution LC1_34 comprising: 1600 ppm chlorine dioxide with 0.2% (v/v) RD3 and RD4
Solution LC2 comprising 800 ppm chlorine dioxide
Solution LC2_1 comprising 800 ppm chlorine dioxide with 0.2% (v/v) RD1
Solution LC2_2 comprising 800 ppm chlorine dioxide with 0.2% (v/v) RD2
Solution LC2_3 comprising 800 ppm chlorine dioxide with 0.2% (v/v) RD3
Solution LC2_4 comprising 800 ppm chlorine dioxide with 0.2% (v/v) RD4
Solution LC2_12 comprising: 800 ppm chlorine dioxide with 0.2% (v/v) RD1 and RD2
Solution LC2_34 comprising: 800ppm chlorine dioxide with 0.2% (v/v) RD3 and RD4

The solutions were prepared in accordance with Examples 2, 2A and 3. RD1 and RD2 signify the anionic surfactants of A spore suspension was generated and counted in accordance with Example 4:

Ribotype 25; $8.0 \times 10^9$ spores/mL ($8.0 \times 10^8$ spores on the glass surface) approximately 80% spores in the suspension.

The glass surfaces were prepared by transferring 0.1 ml of the spore solution to microscopy slides. After the suspension has dried, 0.2 ml of the test solutions were added to the slides for application times between 1 and 10 minutes. Subsequently, the glass surfaces were each placed in a 500 ml glass flask with 250 ml 0.85% NaCl solution and rotated at 200 rpm for 20 minutes.

The results of the cultures in observed CFUs are shown in Table 4, also demonstrating with brackets the number of CFUs in the flask and the number of CFUs in the undiluted PY-broth, representing the number of surviving spores detached from the surface and the number of spores survived not detached from the surface during the rotation, respectively.

In addition to the results of Table 3, it was confirmed that no growth was found in the cultures from the samples taken from the filtrate. Table 3 demonstrates that the spore eliminating efficacy was improved when combing two surfactants with different complementary characteristics when compared to solution comprising a single surfactant.

TABLE 3

|  | Filtration 249 mL | Filtration 1 mL | 0.1 mL From bottle | 0.1 mL Diluted $10^{-1}$ | 0.1 mL Diluted $10^{-2}$ | PY-broth Undiluted | PY-broth Diluted $10^{-2}$ | PY-broth Diluted $10^{-4}$ | Filtration 249 mL |
|---|---|---|---|---|---|---|---|---|---|
| RO-water | overgrown | overgrown | overgrown | overgrown | 292 ($7.3 \times 10^7$) | overgrown | overgrown | 13 ($1.3 \times 10^6$) | 0 |
| 70% ethanol | overgrown | overgrown | overgrown | overgrown | 240 ($6.0 \times 10^7$) | overgrown | overgrown | 86 ($8.6 \times 10^6$) | 0 |
| LC1 | 150 (150) | 0 | 0 | 0 | 0 | 0 | 0 | 0 | 0 |
| LC1_12 | 55 (55) | 0 | 0 | 0 | 0 | 0 | 0 | 0 | 0 |
| LC1_34 | 0 | 0 | 0 | 0 | 0 | 0 | 0 | 0 | 0 |
| LC2 | overgrown | 200 ($5.0 \times 10^4$) | 36 | 2 | 0 | 28 (280) | 0 | 0 | 0 |
| LC2_1 | overgrown | 85 ($2.1 \times 10^4$) | 13 | 0 | 0 | 176 ($1.8 \times 10^3$) | 3 | 0 | 0 |

TABLE 3-continued

|  | Filtration 249 mL | Filtration 1 mL | 0.1 mL From bottle | 0.1 mL Diluted $10^{-1}$ | 0.1 mL Diluted $10^{-2}$ | PY-broth Undiluted | PY-broth Diluted $10^{-2}$ | PY-broth Diluted $10^{-4}$ | Filtration 249 mL |
|---|---|---|---|---|---|---|---|---|---|
| LC2_2 | overgrown | 101 ($2.5 \times 10^4$) | 15 | 2 | 0 | 2 (20) | 0 | 0 | 0 |
| LC2_3 | overgrown | 49 ($1.2 \times 10^4$) | 5 | 0 | 0 | 11 (110) | 0 | 0 | 0 |
| LC2_4 | overgrown | 13 ($3.2 \times 10^3$) | 3 | 0 | 0 | 36 (360) | 0 | 0 | 0 |
| LC2_12 | overgrown | 120 ($3.0 \times 10^4$) | 17 | 1 | 0 | 3 | 0 | 0 | 0 |
| LC2_34 | overgrown | 8 ($2.0 \times 10^3$) | 1 | 0 | 0 | 0 | 0 | 0 | 0 |

EXAMPLE 7

Example 7 outlines a test with different contact for chlorine dioxide solution according to the invention. A spore suspension was generated and counted in accordance with Example 4:

Ribotype 25; $9.6 \times 10^8$ spores/mL ($9.6 \times 10^7$ spores on the glass surface) approximately 80% spores in the suspension.

The glass surfaces were prepared by transferring 0.1 ml of the spore solution to microscopy slides. After the suspension has dried, 0.2 ml of the test solutions were added to the slides for application times between 1 and 10 minutes. Subsequently, the glass surfaces were each placed in a 500 ml glass flask with 250 ml 0.85% NaCl solution and rotated at 200 rpm for 20 minutes.

The test solutions were:
Sterile RO-water 10 min
Ethanol 70% 10 min
Chlorine dioxide 1600 1 min
Chlorine dioxide 1600 2 min
Chlorine dioxide 1600 3 min
Chlorine dioxide 1600 4 min
Chlorine dioxide 1600 5 min
Chlorine dioxide 1600 6 min
Chlorine dioxide 1600 7 min
Chlorine dioxide 1600 8 min
Chlorine dioxide 1600 9 min
Chlorine dioxide 1600 10 min The test solution comprising chlorine dioxide was prepared in accordance with Example 2B, comprising 1600 ppm chlorine dioxide together with 0.2% (v/v) cationic surfactant comprising equal amounts of octyl dimethylamine oxide and lauryl dimethylamine oxide). After rotation, the contents of the flasks were treated and cultured with procedures and agar plates in accordance with Example 4.

The results of the cultures in observed CFUs are shown in Table 4, also demonstrating with brackets the number of CFUs in the flask and the number of CFUs in the undiluted PY-broth, representing the number of surviving spores detached from the surface and the number of spores survived not detached from the surface during the rotation, respectively.

In addition to the results of Table 4, it was confirmed that no growth was found in the cultures from the samples taken from the filtrate.

The results of Table 4 indicate that the test solution is highly efficient for the highly spore contaminated surfaces also at very low contact times. Also at contact times as low as 1 minute, or less test solution provides suitable efficacy to admit chlorine dioxide to a exert spore eliminating effect.

A repeated test based on a spore suspension (Ribotype 25: $4.8 \times 10^8$ spores/mL (. $4.8 \times 10^7$ on the glass surface) about 80% spores in suspension) shows efficacy with as low contact time as 15 seconds with the same test solution.

TABLE 4

|  | Number cfu Filtration 249 mL | Number cfu × 250 Filtration 1 mL | Number cfu × 10 × 250 0.1 mL From bottle | Number cfu × 100 × 250 0.1 mL Diluted $10^{-1}$ | Number cfu × 1000 × 250 0.1 mL Diluted $10^{-2}$ | Number cfu × 10 PY-broth Undiluted | Number cfu × $10^3$ PY-broth Diluted $10^{-2}$ | Number cfu × $10^5$ PY-broth Diluted $10^{-4}$ |
|---|---|---|---|---|---|---|---|---|
| RO-water | overgrown | overgrown | overgrown | overgrown | 171 ($4.3 \times 10^7$) | overgrown | overgrown | 9 ($9.0 \times 10^5$) |
| 70% ethanol | overgrown | overgrown | overgrown | overgrown | 103 ($2.6 \times 10^7$) | overgrown | overgrown | 67 ($6.7 \times 10^6$) |
| $ClO_2$ 1 min | 27 | 1 | 0 | 0 | 0 | 0 | 0 | 0 |
| $ClO_2$ 2 min | 23 | 0 | 0 | 0 | 0 | 0 | 0 | 0 |
| $ClO_2$ 3 min | 100 | 0 | 0 | 0 | 0 | 0 | 0 | 0 |
| $ClO_2$ 4 min | 83 | 0 | 0 | 0 | 0 | 0 | 0 | 0 |
| $ClO_2$ 5 min | 95 | 0 | 0 | 0 | 0 | 0 | 0 | 0 |
| $ClO_2$ 6 min | 52 | 0 | 0 | 0 | 0 | 0 | 0 | 0 |
| $ClO_2$ 7 min | 21 | 0 | 0 | 0 | 0 | 0 | 0 | 0 |
| $ClO_2$ 8 min | 105 | 0 | 0 | 0 | 0 | 0 | 0 | 0 |

TABLE 4-continued

| | Number cfu Filtration 249 mL | Number cfu × 250 Filtration 1 mL | Number cfu × 10 × 250 0.1 mL From bottle | Number cfu × 100 × 250 0.1 mL Diluted $10^{-1}$ | Number cfu × 1000 × 250 0.1 mL Diluted $10^{-2}$ | Number cfu × 10 PY-broth Undiluted | Number cfu × $10^3$ PY-broth Diluted $10^{-2}$ | Number cfu × $10^5$ PY-broth Diluted $10^{-4}$ |
|---|---|---|---|---|---|---|---|---|
| $ClO_2$ 9 min | 153 | 3 | 0 | 0 | 0 | 0 | 0 | 0 |
| $ClO_2$ 10 min | 50 | 1 | 0 | 0 | 0 | 0 | 0 | 0 |

EXAMPLE 8

Example 9 outlines a test with chlorine dioxide solutions of 800 and 1600 ppm having different concentration of surfactants made in accordance with Example 2A. A spore suspension was generated and counted in accordance with Example 4:

Ribotype 25; $8.0 \times 10^8$ spores/mL ($8.0 \times 10^7$ spores on the glass surface) approximately 80% spores in the suspension.

The glass surfaces were prepared by transferring 0.1 ml of the spore solution to microscopy slides. After the suspension has dried, 0.2 ml of the test solutions were added to the slides for an application time of 2 minutes. Subsequently, the glass surfaces were each placed in a 500 ml glass flask with 250 ml 0.85% NaCl solution and rotated at 200 rpm for 20 minutes.

The test solutions were:
Sterile RO-water
Ethanol 70%
LC1A_2 comprising 1600 ppm chlorine dioxide
LC1B_2 comprising 1600 ppm chlorine dioxide with 2% (v/v) RD3 and RD4
LC1C_2 comprising 1600 ppm chlorine dioxide with 0.02% (v/v) RD3 and RD4
LC1E_2 comprising 1600 ppm chlorine dioxide with 0.2% (v/v) RD3 and RD4
LC2A_2 comprising 800 ppm chlorine dioxide
LC2B_2 comprising 800 ppm chlorine dioxide with 2% (v/v) RD3 and RD4
LC2C_2 comprising 800 ppm chlorine dioxide with 0.02% (v/v) RD3 and RD4
LC2E_2 comprising 800 ppm chlorine dioxide with 0.2% (v/v) RD3 and RD4

RD3 and R4 signify, the cationic surfactants of Example 2A Macat(RTM) AO-8 and Macat(RTM) AO-12.

After rotation, the contents of the flasks were treated and cultured with procedures and agar plates in accordance with Example 4.

The results of the cultures in observed CFUs are shown in Table 5, also demonstrating with brackets the number of CFUs in the flask and the number of CFUs in the undiluted PY-broth, representing the number of surviving spores detached from the surface and the number of spores survived not detached from the surface during the rotation, respectively.

In addition to the results of Table 5, it was confirmed that no growth was found in the cultures from the samples taken from the filtrate.

Table 5 demonstrates that a chlorine dioxide solution concentration of 0.2% (v/v) has the more advantageous performance to eliminate spores on surfaces, compared both to higher and lower concentrations of surfactant at both tested strengths of chlorine dioxide (800 and 1600 ppm). The results also confirm the efficacy of the present surfactant to assist chlorine dioxide to exert its eliminating effect.

TABLE 5

| | Number cfu Filtration 249 mL | Number cfu × 250 Filtration 1 mL | Number cfu × 10 × 250 0.1 mL From bottle | Number cfu × 100 × 250 0.1 mL Diluted $10^{-1}$ | Number cfu × 1000 × 250 0.1 mL Diluted $10^{-2}$ | Number cfu × 10 PY-broth Undiluted | Number cfu × $10^3$ PY-broth Diluted $10^{-2}$ | Number cfu × $10^5$ PY-broth Diluted $10^{-4}$ | Number cfu × $10^5$ Filtration 249 mL |
|---|---|---|---|---|---|---|---|---|---|
| RO-water | overgrown | overgrown | overgrown | overgrown | | 97 ($2.4 \times 10^7$) | overgrown | 61 ($6.1 \times 10^4$) | 0 |
| 70% ethanol | overgrown | overgrown | overgrown | overgrown | | 81 ($2.0 \times 10^7$) | overgrown | overgrown | 28 ($2.8 \times 10^6$) |
| LC1A_2 | overgrown | 98 ($2.4 \times 10^4$) | 13 | 2 | | 0 | overgrown | 23 ($2.3 \times 10^4$) | 0 |
| LC1B_2 | overgrown | 74 ($1.8 \times 10^4$) | 6 | 0 | | 0 | overgrown | 28 ($2.8 \times 10^4$) | 0 |
| LC1C_2 | overgrown | 20 ($5.0 \times 10^3$) | 4 | 0 | | 0 | overgrown | 8 ($8.0 \times 10^3$) | 0 |
| LC1E_2 | overgrown | 8 ($2.0 \times 10^3$) | 0 | 0 | | 0 | overgrown | 10 ($1.0 \times 10^4$) | 0 |
| LC2A_2 | overgrown | overgrown | overgrown | 29 ($7.2 \times 10^5$) | | 0 | overgrown | 287 ($2.9 \times 10^5$) | 4 |
| LC2B_2 | overgrown | overgrown | 150 ($3.8 \times 10^5$) | 9 | | 0 | overgrown | 136 ($1.4 \times 10^5$) | 0 |
| LC2C_2 | overgrown | overgrown | overgrown | 23 ($5.8 \times 10^5$) | | 2 | overgrown | 129 ($1.3 \times 10^5$) | 1 |
| LC2E_2 | overgrown | overgrown | overgrown | 35 ($8.8 \times 10^5$) | | 3 | overgrown | 96 ($9.6 \times 10^4$) | 1 |

The invention claimed is:

1. An acidic aqueous composition having an acidic pH of from about 1 to about 4, for elimination of spores of spore forming bacteria, comprising from about 100 to about 2000 ppm dissolved chlorine dioxide, and a surfactant system having a wetting effect and a spore solubilising effect, wherein the surfactant system comprises at least two hydrocarbon ionic surfactants stable against oxidation at the acidic pH and wherein one surfactant is octyldimethylamine oxide and one surfactant is lauryldimethylamine oxide.

2. The composition according to claim 1, wherein the at least two surfactants are present in amount of from about 0.01 to about 2% (v/v).

3. The composition according to claim 1, wherein the amount of surfactants is about 0.2% (v/v) and comprises essentially equal amounts of octyldimethylamine oxide and lauryldimethylamine oxide.

4. A method of eliminating spores of spore forming bacteria on a surface by contacting the surface with a sufficient amount of a composition according to claim 1.

5. Method according to claim 4, wherein the spore forming bacteria belongs to genus *Clostridium*.

6. Method according to claim 4, wherein the spore forming bacteria comprises *Clostridium difficile*.

7. The composition according to claim 1, comprising from about 300 to about 2000 ppm dissolved chlorine dioxide.

8. The composition according to claim 1, comprising from about 400 to about 2000 ppm dissolved chlorine dioxide.

9. The composition according to claim 1, comprising from about 500 to about 2000 ppm dissolved chlorine dioxide.

* * * * *